United States Patent [19]
Derrieu et al.

[11] Patent Number: 6,010,720
[45] Date of Patent: Jan. 4, 2000

[54] COMPOSITION AND SYSTEM FOR ORAL ADMINISTRATION TO ANIMALS

[75] Inventors: Guy Derrieu, Cagnes-Sur-Mer; Bernard Raynier, Nice; Jean-Luc Pougnas, Cagnes-sur-Mer; Luc Castelli, Saint Laurent du Var, all of France

[73] Assignee: Laboratories Virbac, Carros, France

[21] Appl. No.: 08/615,285

[22] PCT Filed: Sep. 27, 1994

[86] PCT No.: PCT/FR94/01120

§ 371 Date: May 22, 1996

§ 102(e) Date: May 22, 1996

[87] PCT Pub. No.: WO95/08931

PCT Pub. Date: Apr. 6, 1995

[30] Foreign Application Priority Data

Sep. 27, 1993 [FR] France .................................... 93 11449

[51] Int. Cl.[7] ............................... A61K 9/10; A61K 9/16; A61K 47/32
[52] U.S. Cl. ............................. 424/486; 424/501
[58] Field of Search .................................... 424/484, 486, 424/410, 408, 501, 84

[56] References Cited

U.S. PATENT DOCUMENTS 5,169,645  12/1992  Shukla et al. .

FOREIGN PATENT DOCUMENTS

WO 89/12393  12/1989  WIPO .

*Primary Examiner*—Edward J. Webman
*Attorney, Agent, or Firm*—Oblon, Spivak, McClelland, Maier & Neustadt, P.C.

[57] ABSTRACT

Composition and system for oral administration of chemicals or medicaments, and applications thereof (for example as medicament, dietetic product, food product, bait). Said composition comprises essentially (a) from 3% to 20% by weight of at least one water-insoluble polymer selected from the polyamides and ethylene copolymers such as ethylene/vinyl acetate; (b) from 35% to 60% by weight of lipidic substances, at least one of these lipidic substances being solid at room temperature, the melting point of the solid lipidic substance(s) being lower than that of the polymer(s); (c) from 5% to 45% of at least one paletable substance; (d) from 0% to 50% of another suitable complementary ingredient. Said composition can be obtained by (i) melting of the solid lipidic substances at a temperature lower than the melting point of the polymer(s), and (ii) mixing of the polymer(s) and the other constituents at the same temperature as for (i). A method of preparing said systems and composition is also disclosed.

25 Claims, No Drawings

COMPOSITION AND SYSTEM FOR ORAL ADMINISTRATION TO ANIMALS

The present invention relates to a composition and to a system designed to allow the oral administration of chemicals or medicaments, such as vitamins, trace elements, amino acids, nutritional substances, vaccines and the like, to domestic or wild animals, such as mammals, fish, crustacea, and the like.

The present invention also relates to the method for producing the said systems and compositions.

Systems which allow the oral administration of medicaments to domestic animals, so as to avoid the parenteral route, which requires restraining the animal, are already known. Systems capable of treating animals raised extensively or wild animals, which are difficult or dangerous to restrain, are also known.

Such systems are the subject of Patent Applications or Patents (Patent EP 0 240 826, Patent EP 0 208 528 and Patent Application EP 0 421 863).

The bait described in Patent EP 0 240 826 is obtained by a first casting, at the bottom of a mould, of a support, comprising a lipid compound (having a melting point of between 20° and 60° C.), a compound designed to stabilize the shape of the bait and an attractive and palatable compound for the animals, introducing the active substance on the solidified support layer, under a second casting of the said support, so as to completely cover the said active substance.

This system has the disadvantage of exhibiting low mechanical strength and brittleness in the vicinity of the junction of the two castings and makes it unsuitable for large-scale distribution methods (aerial release, for example, for treating large numbers of wild animals, over large areas).

Patent EP 208 528 describes a bait for fish and crustacea consisting essentially of a water-insoluble polymer having a melting point of less than 110° C. (polyamides or ethylene copolymers, EVA, in particular), of an attractive substance and of edible oil or of molasses (0 to 20%).

The baits according to this Patent EP 208 528 are obtained by extrusion at 90–110° C. of a dry mixture of the polymer, the attractive substance and optionally the edible oil.

International Application WO 89/12393 describes pesticidal compositions comprising EVA, a bioactive agent, a source of proteins/sugars/lipids and optionally 0 to 20% edible oil, an attractive substance, a colorant, a preservative, a repelling agent and a biomarker.

The compositions according to this International Application PCT WO 89/12393 may be in the form of blocks or of tablets and are also prepared by extrusion of the above-mentioned composition, either by melting the polymer (fused melt at a temperature <110° C.) followed by the mixing of the latter with other ingredients, or by heating, up to the melting point of the polymer, a mixture of all the ingredients in a dry form.

Patent Application EP 421 863 describes systems comprising two parts: an envelope in tubular form, obtained by extrusion and comprising at least one attractive substances, at least one agglomerating substance (polysaccharides, starches or polymers such as EVA) and optionally a hydrophobic substance (oil) and inside the cavity of the envelope, a binding substance (mixture of fatty substances having a melting point which is not too high) containing an active ingredient, the binding substance taking the internal shape of the envelope. Such an envelope has a high mechanical and thermal strength which allows, in particular, distribution by aerial release.

The various systems obtained by extrusion exhibit, however, a number of disadvantages:

coating the particles of active substances with the polymer (WO 89/12393), which modifies their rate of release of these substances; in addition, such coated food particles are poorly assimilated, because of a poor assimilation of the polymers (resistance to enzymes in particular), selection of the polymers necessarily from among those whose melting point is <110° C. (EP 208 528, EP 421 863), multiplicity of the operations (EP 421 863: formation of two different components, which are then joined together: heterogeneous system or EP 0 240 826), a texture which is rigid to a greater or lesser extent and which does not withstand aerial release and/or extreme temperature conditions.

The aim of the present invention is, consequently, to provide a composition and a system which are more suitable for the requirements of practical use than the compositions and systems of the prior art, especially:

in that they are easy to produce, in that they are homogeneous, in that they have an elastic texture, which is particularly highly suitable for large-scale distribution, especially by aerial release under various climatic conditions, in that they exhibit a high mechanical strength and a high thermal resistance, allowing, depending on the bioactive subtance(s) to be administered, preservation at temperatures of between −30° C. and +50° C., in that they withstand such extreme temperatures without modification of their texture and especially without lipid exudation, in that they are particularly highly suitable for oral administration of substances with a therapeutic, dietetic or dietary effect and the like, in animals, in that they are attractive and palatable for the animal in question and therefore exhibit a texture acceptable for the animal, for example a nonsticky texture, thus ensuring effective consumption of the bioactive substance, and in that they are stable (shape and size not altered during a prolonged stay in the distribution medium), more particularly for wild animals or for animals produced by extensive breeding.

The aim of the present invention is also to provide a method for preparing the said systems and compositions, which is easy to use, which is inexpensive and which can be automated.

The subject of the present invention is a palatable composition in solid form, of the type comprising at least one water-insoluble polymer, an attractive substance and lipid source, which composition is characterized in that it comprises essentially:

(a) between 3% and 20% by weight of at least one water-insoluble polymer chosen from synthetic polyamides and ethylene copolymers, (b) between 35 and 60% by weight of lipid substances, at least one of these lipid substances being in solid form at room temperature, the melting point of the lipid substance(s) in solid form being less than that of the polymer(s), and (c) between 5 and 45% of at least one palatable substance and (d) between 0 and 50% of another suitable additional ingredient and in that it can be obtained by:

(i) melting of the lipid substances in solid form at a temperature less than that of the melting point of the polymer(s), and (ii) mixing of the polymer(s) and the other constituents at the same temperature as in (i).

Owing to an advantageous embodiment of the said composition, it can be obtained by:

(i) melting of the lipid substances in solid form at a temperature of between 40° and 80° C., and (ii) mixing of the polymer(s) and of the other constituents in the same temperature range.

Unexpectedly, a composition comprising, in combination, at least one water-insoluble polymer, at least one lipid substance and at least one palatable substance and obtained by melting the lipid substances in solid form at a temperature less than the melting temperature of the polymers, makes it possible to obtain a composition of homogeneous texture and with an "almond paste" type consistency, which does not modify the rate of release of the active substances which it may, in addition, contain and which is particularly highly suitable, by virtue of its mechanical qualities (elasticity, good behaviour and the like) and thermal qualities, for the desired applications.

Also unexpectedly, in spite of the large quantity of lipid substances, no exudation of lipids is observed between −30° C. and +50° C. (extreme climatic conditions), because of this particular texture, in which the polymer is dispersed, that is to say "embedded" so to speak, this being in particular due to the presence of a palatable substance.

The specific mode of preparation of the said composition makes it possible, in addition, to artificially increase the overall melting point of the composition, without modifying its assimilation qualities.

The polymer is advantageously an ethylene/vinyl acetate copolymer (EVA), comprising between 8 and 60% vinyl acetate groups.

According to another advantageous embodiment of the said composition, it comprises up to 50% by weight of bioactive substance.

According to another advantageous embodiment of the said composition, it optionally comprises at least one of the following additional ingredients (d): preservatives, antioxidants, colorants, conventional binders such as starches, celluloses, animal, plant or synthetic waxes, silicones, long-chain fatty acids, tracers, one or more sweeteners, surfactants, surface-active agents and unmoulding agents.

The term "lipid substance" includes, but with no limitation being implied, the following compounds:

a) natural origin:
beeswax, lanolin, lard, pig, beef or fish fats; fish oil (animal origin); Carnauba wax, soya bean, groundnut and rapeseed oils (plant origin); paraffin, microcrystalline wax, petroleum jelly, mineral oils (inorganic origin);

b) semisynthetic or synthetic origin:
fatty alcohols (cetyl alcohol), fatty acids (stearic, palmitic acid), fatty acid and alcohol esters (white wax), polyoxyethylenated vegetable oils (Labrafils®, Gattefosse), hydrogenated vegetable oils (Cutina ® HR, Henkel), mono-, di- or triglycerides of fatty acids (Softisan® 154, Dynamit Nobel).

The polymer(s) should be provided in the form of a powder, as fine as possible, for example between 10 and 400 micrometres.

The palatable substance(s) may be natural or synthetic, such as meat or fish meals, or vegetable meals, flavourings and the like.

Preferably, the composition in accordance with the invention comprises a palatable substance in liquid form, a liquid fish flavouring for example (with the characteristic of a solvent for the lipid substances) and a palatable substance in solid form, such as a meat or fish meal (with the characteristic of a binder).

The subject of the present invention is also a system for the oral administration of at least one bioactive substance to animals, characterized in that it consists of a composition as defined above, made in the form of blocks or of granules.

A block is of any configuration (cylindrical, parallelepipedic and the like) and weighs between 1 and 50 g.

Granules with a cylindrical or spherical configuration to a greater or lesser extent weigh from 0.2 to 2 g.

Advantageously, the system in block form includes the bioactive substance(s) in the above composition.

As variant, the said blocks enclose or envelop the said bioactive substance(s); in this case, the said bioactive substance is not included in the composition in accordance with the invention, but is at the centre of the said block.

In the latter case, the bioactive substance(s) are provided in a solid form such as tablets, oral freeze-dried products and the like, or are provided in liquid or pasty form and may be contained especially in sachets, gelatin capsules, capsules and the like.

The subject of the present invention is also a method for preparing a composition in accordance with the invention, characterized in that it comprises:

(i) the melting of the lipid substances in solid form, at a temperature less than the melting temperature of the polymer(s) of the said composition and (ii) the mixing of the polymer(s) and of the other constituents at the same temperature.

According to an advantageous embodiment of the said method, the said temperature is between 40 and 80° C.

The subject of the present invention is also a method for preparing the said systems, characterized in that it comprises:

(1) the preparation of a composition in accordance with the invention by:
(i) melting the lipid substances in solid form, at a temperature less than the melting temperature of the polymer(s) of the said composition and
(ii) mixing the polymer(s) and the other constituents at the same temperature; and (2) the appropriate shaping of the compositions obtained in (1).

According to an advantageous embodiment of this method, the said temperature is between 40 and 80° C.

According to another advantageous embodiment of this method, the shaping stage is performed by moulding.

According to another advantageous embodiment of this method, the shaping stage is performed by injection.

When the said systems are shaped by moulding or injection, they are advantageously in the form of blocks.

In accordance with the invention, when the said systems are in the form of blocks, the bioactive substance(s) may be enclosed in the said blocks, as specified above.

In this case, (a) a part of the said composition in accordance with the invention is distributed into a mould of appropriate conformation, (b) the bioactive substance(s) are then introduced, and then (c) the remainder of the said composition is introduced into the mould.

Because of the specific texture of the composition in accordance with the invention, a system produced in this manner does not exhibit any brittleness at the junction of the two parts of the composition.

According to another advantageous embodiment of the said method, the shaping stage is performed by granulation.

Advantageously, the said granules are obtained by converting the composition of "almond paste" texture, by passing through a cooling tower via a vibrating plate with calibrated orifices in order to obtain directly homogeneous granules of 0.2 to 2 g.

This temperature range makes it possible to envisage the use of active substances which are even sensitive to heat.

This temperature is much lower than the melting temperature of the polymer(s) used.

The addition of at least 3% polymer(s) and/or copolymer(s) and of at least one palatable substance, to the hot mixture, is between 40 and 80° C., and shaping, without requiring conventional conversion of the usual polymers used (melting), makes it possible contrary to what is known in the prior art, to obtain unexpectedly, as specified above, a system having the following properties:

- heat resistance: the addition of the polymer(s) greatly increases the melting point of the lipid constituents by avoiding exudation of the latter and the disintegration of the device;
- elasticity, the addition of the polymer(s), combined with the palatable substance, greatly increases the resistance to shock;
- integrity: between −30° C. and 50° C., the system is not subjected to any deterioration of its appearance, cracks, division, exudation and the like, any loss of its physical or organoleptic properties once it has returned to a normal temperature (20–25° C.);
- attractive and palatable;
- a texture which is acceptable by the animal: conversion, mixing and shaping at 40–80° C., a temperature well below the melting point of the polymer(s) used, generate an appearance and a texture which are particularly suitable for the effective consumption of the system by the animals;
- possibility of having any conceivable shapes and sizes depending on the target animal species and depending on the conformation mould used;
- possibility of being ground for example by cryogenics;
- possibility, by avoiding distribution, of converting the homogeneous mixture at 40–80° C. to granules of 0.2 to 2 g, through a vibrating plate perforated with calibrated orifices, connected to a cooling tower, 30 cm to 10 m high, whose atmosphere is controlled, optionally inert; this equipment ensures a homogeneous distribution of the granules.

The system in accordance with the invention finds application especially as medicament, dietetic product, food composition or bait.

In addition to the preceding arrangements, the invention further comprises other arrangements, which will emerge from the description below, which refers to exemplary embodiments of the method which is the subject of the present invention.

It should be understood, however, that these examples are given solely by way of illustration of the subject of the invention and do not constitute, in any manner, a limitation thereto.

EXAMPLE 1

2.5 g Unit Food Supplement for Dogs

Copra oil and paraffin which are liquefied at 70° C. are introduced into a heating planetary mixer. All the other constituents are introduced according to the following composition (unit formula), with stirring, while the temperature is maintained at 70° C.

| lipid substances: | |
|---|---|
| copra oil | 27.5% |
| paraffin (50–52° C.) | 22.5% |
| insoluble polymer: | |
| ethylene/vinyl acetate* | 10% |
| palatable substance: | |
| meat meal | 5% |
| beef flavouring | 2% |
| active ingredients: | |
| dicalcium phosphate | 20% |
| vitamins A, $D_3$, E, $B_1$, $B_2$, PP | 6% |
| amino acids | 6% |
| trace elements | 1% |

*with 28% vinyl acetate.

The mixture is homogenized for ½ an hour while the temperature is maintained. The preparation is then distributed into oblong PVC cells previously thermoformed at the rate of 2.5 g per cell. The filled cells are then cooled by passing through a refreezing tunnel (−10° C.), and closed by seaming an aluminium film.

EXAMPLE 2

Tests in Vitro and in Vivo of the Systems in Accordance With the Invention Which are Obtained in Example 1 a) Temperature Characteristics:

The tests showed that at temperatures of between −30° C. and +50° C., there was no modification of the appearance or of the structure. Thus, the system, when placed on an absorbent paper stored at 45° C., softens very slightly but does not show any exudation, and does not cause any fat stain on the absorbent paper.

The same is not true for systems whose composition has been modified (replacement of 10% ethylene/vinyl acetate by 10% paraffin (50–52° C.)): high softening of the systems, they are greasy, difficult to handle and leave greasy stains on the absorbent paper.

b) Attractiveness and Palatability:

The tests were performed on three groups of six dogs (six small, six medium and six big) assigned to individual boxes. At the end of the meal, two systems are presented to each dog in a bowl. A complete consumption is noted. The test is repeated a quarter of an hour later; the consumption is still total.

This test was also carried out with systems stored in part at −27° C. and in part at +45° C. for one month, and then collected at room temperature and presented to the animals. No modification in the consumption and the absorption of the system was noted.

c) Stability:

A study of stability of the vitamins was carried out on samples stored in thermoformed cells, closed with a seamed aluminium film in a cardboard box at room temperature (20–25° C.) and in daylight for one year. No notable loss of the vitamin content was noted.

EXAMPLE 3

Vaccinating Bait for Dogs.

Beef tallow and paraffin which are liquefied at 55° C. are introduced into a heating planetary mixer. All the other constituents are introduced according to the following composition (unit formula) with stirring, while the temperature is maintained at about 55° C.

| lipid substances: | |
|---|---|
| paraffin (50–52° C.) | 20% |
| beef tallow | 30% |
| insoluble polymer: | |
| ethylene/vinyl acetate* | 10% |
| palatable substances: | |
| fish meal | 30% |
| liquid fish flavouring | 10% |

*with 28% vinyl acetate.

The mixture is homogenized for ½ an hour while the temperature is maintained. The preparation is then distributed once in square PVC moulds of sides 50 mm and depth 15 mm, previously thermoformed in an amount of about 8 g per cell. The partially filled cells are then cooled down to about 30° C. and a blister pack 25 mm in diameter and 5 mm thick containing the vaccinal solution is placed over the first casting.

The mixture is distributed a second time at 50° C. in order to obtain a bait with a final weight close to 31 g, which immobilizes the blister pack at the centre of the device which then appears as a homogeneous block which is passed through a freezing tunnel (−30° C.) in order to cool the system but also to maintain the integrity of the vaccine. The system obtained in the form of a bait is then unmoulded and stored at −30° C. It exhibits no brittleness at the junction of the two castings because the second casting is performed while the first is still hot.

EXAMPLE 4

The tests performed in Example 2 were repeated with systems obtained according to Example 3.

The blister packs obtained at the centre of the systems were filled with a Rhodamine B staining solution which is used as marker.

The systems had been stored for one month at −27° C. before the experiment. A frozen system was placed in each cage; 24 hours later, the disappearance of the systems was noted and all the animals had a coloured mouth.

These results show good attractiveness within the 24 hours following the distribution and a structure which promotes consumption. The freezing does not adversely affect consumption but allows optimum preservation of the vaccinal solutions.

Systems produced according to Example 3, and systems whose composition had been modified (replacement of the 10% ethylene/vinyl acetate by 10% paraffin (50–52° C.)), stored at 20–25° C. and frozen (−27° C.) were released by aeroplane from an altitude of about 130 meters, over a concrete runway of an airfield. No system produced according to the invention was ruptured with separation between the blister pack and the support, and no blister pack was perforated, whereas the systems produced without copolymer had numerous cases of damage.

EXAMPLE 5

Medicine for Fishes in the Form of 0.5 g Granules.

Paraffin which is liquefied at 55° C. is introduced into a heating planetary mixer.

All the other constituents are introduced according to the following composition (unit formula), with stirring, while the temperature is maintained at about 55° C.:

| lipid substances: | |
|---|---|
| fish oil | 10% |
| paraffin (50–52° C.) | 37% |
| insoluble polymer: | |
| ethylene/vinyl acetate* | 17% |
| palatable substance: | |
| fish meal | 32% |
| active ingredients: | |
| oxolinic acid | 0.5% |
| vitamins A, $D_3$, E, $B_1$, $B_2$, $B_6$ | 2.5% |
| trace elements | 1% |

*with 28% vinyl acetate

The mixture is homogenized for ½ an hour while the temperature is maintained. The hot homogeneous mixture is converted to 0.5 g granules, through a vibrating plate perforated with calibrated orifices, connected to a cooling tower, 3 m high, whose atmosphere is maintained at about 0° C.

As evident from the above, the invention is not in the least limited to those of its embodiments, implementations and applications which have just been described more explicitly; it embraces on the contrary all the variants which may occur to the specialist in this field, without departing from the framework or the scope of the present invention.

We claim:

1. Palatable composition in solid form, comprising:
   (a) between 3% and 20% by weight of at least one water-insoluble polymer selected from the group consisting of synthetic polyamides and ethylene/vinyl acetate copolymers,
   (b) between 35 and 60% by weight of lipid substances, at least one of these lipid substances being in solid form at 20–25° C., the melting point of the lipid substance(s) in solid form being less than that of the polymer(s), and
   (c) between 5 and 45% of at least one palatable substance and
   (d) between 0 and 50% of an additional ingredient
   wherein said palatable composition is obtained by:
   (i) melting of the lipid substances in solid form at a temperature less than that of the melting point of the polymer(s), and
   (ii) mixing of the polymer(s) and the other constituents at the same temperature as in (i).

2. Composition according to claim 1, characterized in that it can be obtained by:
   (i) melting of the lipid substances in solid form at a temperature of between 40° and 80° C., and
   (ii) mixing of the polymer(s) and of the other constituents in the same temperature range.

3. Composition according to claim 1, characterized in that it comprises up to 50% by weight of bioactive substance.

4. Composition according to claim 1, further comprising at least one additional ingredient selected from the group consisting of preservatives, antioxidants, colorants, binders, tracers, one or more sweeteners, surfactants and unmoulding agents.

5. Composition according to claim 1, characterized in that the palatable substance is selected from the group consisting of liquid flavourings and meals.

6. System for the oral administration of at least one bioactive substance to animals, characterized in that it consists of a composition according to claim 1, made in the form of blocks.

7. System for the oral administration of at least one bioactive substance to animals, characterized in that it consists of a composition according to claim 1, made in the form of granules.

8. System according to claim 6, characterized in that the bioactive substance(s) are included in the composition constituting the said blocks.

9. System according to claim 6, characterized in that the bioactive substance(s) are enclosed in the said blocks.

10. Method for preparing a composition according to claim 1, characterized in that it comprises:
   (i) the melting of the lipid substances in solid form, at a temperature less than the melting temperature of the polymer(s) of the said composition and
   (ii) the mixing of the polymer(s) and of the other constituents at the same temperature.

11. Method according to claim 10, characterized in that the said temperature is between 40 and 80° C.

12. Method for preparing a system for the oral administration of at least one bioactive substance to an animal wherein the system comprises the composition of claim 1 in the form of blocks or granules, comprising the steps of:
   (1) the preparation of a composition according to claim 1 by:
      (i) melting the lipid substances in solid form, at a temperature less than the melting temperature of the polymer(s) of the said composition and
      (ii) mixing the polymer(s) and the other constituents at the same temperature; and
   (2) shaping the compositions obtained in (1).

13. Method according to claim 12, characterized in that the said temperature is between 40 and 80° C.

14. Method according to claim 12, characterized in that the shaping stage is performed by moulding.

15. Method according to claim 12, characterized in that the shaping stage is performed by injection.

16. Method according to claim 14, characterized in that the said systems are provided in the form of blocks.

17. Method according to claim 12, characterized in that the shaping stage is performed by granulation.

18. The system of claim 6 in the form of a medicament, a dietetic product, a food product or bait.

19. The system of claim 7 in the form of a medicament, a dietetic product, a food product or bait.

20. Composition according to claim 1, wherein said water-insoluble polymer is a synthetic polyamide.

21. Composition according to claim 1, wherein said water-insoluble polymer is an ethylene/vinyl acetate copolymer.

22. Method according to claim 10, wherein said water-insoluble polymer is a synthetic polyamide.

23. Method according to claim 10, wherein said water-insoluble polymer is an ethylene/vinyl acetate copolymer.

24. Method according to claim 12, wherein said water-insoluble polymer is a synthetic polyamide.

25. Method according to claim 12, wherein said water-insoluble polymer is an ethylene/vinyl acetate copolymer.

* * * * *